US009119814B2

(12) United States Patent
Kim et al.

(10) Patent No.: US 9,119,814 B2
(45) Date of Patent: Sep. 1, 2015

(54) COMPOSITION FOR PREVENTION OF INFLUENZA VIRAL INFECTION COMPRISING SUMAC EXTRACT, AIR FILTER COMPRISING THE SAME AND AIR CLEANING DEVICE COMPRISING THE FILTER

(75) Inventors: Hyoung Joon Kim, Seoul (KR); Chan Jung Park, Seoul (KR)

(73) Assignee: WOONGJIN COWAY CO., LTD., Gongju-Si (KR)

(*) Notice: Subject to any disclaimer, the term of this patent is extended or adjusted under 35 U.S.C. 154(b) by 169 days.

(21) Appl. No.: 12/789,331

(22) Filed: May 27, 2010

(65) Prior Publication Data

US 2011/0086118 A1    Apr. 14, 2011

Related U.S. Application Data

(60) Provisional application No. 61/251,674, filed on Oct. 14, 2009.

(51) Int. Cl.
    *A61K 36/16*     (2006.01)
    *A61L 9/01*     (2006.01)
    *B01D 46/00*     (2006.01)
    *B01D 53/34*     (2006.01)

(52) U.S. Cl.
    CPC . *A61K 36/16* (2013.01); *A61L 9/01* (2013.01); *B01D 46/0028* (2013.01); *B01D 53/34* (2013.01); *A61L 2209/14* (2013.01); *B01D 2257/91* (2013.01); *B01D 2259/4508* (2013.01); *B01D 2259/4541* (2013.01); *B01D 2259/4566* (2013.01)

(58) Field of Classification Search
None
See application file for complete search history.

(56) References Cited

U.S. PATENT DOCUMENTS

| | | | |
|---|---|---|---|
| 5,411,733 A | 5/1995 | Hozumi et al. | |
| 6,267,993 B1 * | 7/2001 | Kadono et al. | 424/769 |
| 2007/0299040 A1 | 12/2007 | Yoon | |
| 2011/0085992 A1 | 4/2011 | Kim et al. | 424/58 |
| 2011/0126501 A1 | 6/2011 | Kim et al. | 55/524 |

FOREIGN PATENT DOCUMENTS

| | | |
|---|---|---|
| CN | 1207309 A | 2/1999 |
| JP | 2002-316909 A | 10/2002 |
| JP | 2005-028269 A | 2/2005 |
| JP | 2005-125141 A | 5/2005 |
| JP | 2007-144772 | 6/2007 |
| JP | 2008-002516 | 1/2008 |
| KR | 2008088900 A * | 10/2008 |
| WO | WO 97/00679 A1 | 1/1997 |
| WO | WO 2006011541 A1 * | 2/2006 |
| WO | WO 2007/016223 A2 | 2/2007 |
| WO | WO 2010/047550 A2 | 4/2010 |

OTHER PUBLICATIONS

"OSHA: Pandemic Influenza Preparedness and Response Guidance for Healthcare Workers and Healthcare Employers". 2009 [Retrieved from the Internet: Sep. 21, 2011]. Retreived from the Internet: <URL: http://www.osha.gov/Publications/OSHA_pandemic_health.pdf>.*
Rowe, J. "Rhus Clan". Web publication date: Apr. 7, 1999 [Retrieved from the Internet on: Sep. 21, 2011]. Retrieved from the Internet: <URL: http://www.ibiblio.org/london/permaculture/mailarchives/permaculture-UNC/msg00943.html>.*
Coway. "Flu Season Brings Increased Attention to Coway Flu Fighting Air Purifier". Article Date: Sep. 19, 2009 [Retrieved from the Internet on: Mar. 19, 2012]. Retrieved from the Internet: <URL: http://www.coway-usa.com/board/bbs/board.php?bo_table=News%wr_id=10>.*
"Rhus tox" . Internet Archive Date: Jan. 10, 2004 [Retrived from the Internet on: Aug. 25, 2014]. Retrieved from: <URL: https://web.archive.org/web/20040110135630/http://www.herbs2000.com/homeopathy/rhus_tox.htm>.*
Chan-Jung et al., XP-002609224, AN 2009-E98205, Oct. 6, 2008, 1 page.
Dawood et al., "Emergence of a Novel Swine-Origin Influenza A (H1N1) Virus in Humans," *The New England Journal of Medicine* 360(25):2605-2615, 2009.
Extended European Search Report for European Application No. 10005580.5, dated Feb. 7, 2011, 7 pages.
Lin et al., "Antiviral Activities of Biflavonoids," *Planta Medica* 65:120-125, 1999.
Miki et al., "Anti-influenza virus activity of biflavonoids," *Bioorganic & Medicinal Chemistry Letters* 17:772-775, 2007.
Rayne et al., "Biological Activities of Extracts from Sumac (*Rhus* spp.): A Review," *Plant Foods Hum Nutr* 62:165-175, 2007.
Webster et al., "H5N1 Influenza—Continuing Evolution and Spread," *N Engl J Med* 355(21): 2174-2177, 2006.
Zakarjan, "Aromatic Balsam," XP002618725, Database accession No. BG96722, Jul. 28, 1995, 1 page.
Dawood et al., "Emergence of a Novel Swine-Origin Influenza A (H1N1) Virus in Humans," *The New England Journal of Medicine* 360(25):2605-2615, Jun. 18, 2009.
Webster et al., "H5N1 Influenza—Continuing Evolution and Spread," *The New England Journal of Medicine* 355(21):2174-2177, Nov. 23, 2006.
Yasuyuki, O., "Development of 'AI filter' as an inhibiting filter against Avian Influenza Virus," Nonwovens Review, vol. 76, pp. 5-7, Jun. 2007 (w/ English abstract).
World Health Organization, "Characteristics of the emergent influenza A (H1N1) viruses and recommendations for vaccine development," 6 pages, 2009.

* cited by examiner

*Primary Examiner* — Amy L Clark
(74) *Attorney, Agent, or Firm* — Seed IP Law Group PLLC

(57) ABSTRACT

Disclosed are a composition for the prophylaxis of influenza viral infection comprising a sumac extract, an air filter coated with the same, and an air cleaner comprising the air filter. Having high inhibitory activity against influenza virus, the composition comprising a sumac extract can be applied to the prevention of influenza viral infection. Also, the filter coated with the composition can remove influenza viruses from the air so that it can be employed in an air cleaner for the prophylaxis of influenza viral infection.

10 Claims, No Drawings

COMPOSITION FOR PREVENTION OF INFLUENZA VIRAL INFECTION COMPRISING SUMAC EXTRACT, AIR FILTER COMPRISING THE SAME AND AIR CLEANING DEVICE COMPRISING THE FILTER

CROSS-REFERENCE TO RELATED APPLICATION

This application claims the benefit under 35 U.S.C. §119(e) of U.S. Provisional Patent Application No. 61/251,674 filed Oct. 14, 2009, which application is incorporated herein by reference in its entirety.

BACKGROUND OF THE INVENTION

1. Field of the Invention

The present invention relates to a composition for the prophylaxis of influenza viral infection, comprising a sumac extract, an air filter comprising the same, and an air cleaner comprising the air filter.

2. Description of the Related Art

Influenza, commonly referred to as the flu, is an infectious disease caused by RNA viruses of the family Orthomyxoviridae. The most common symptoms of the disease are chills, fever, sore throat, muscle pains, a severe headache, coughing, weakness/fatigue and general discomfort. Fever and coughing are the most frequent symptoms. In more serious cases, influenza causes complications which can be fatal.

Typically, influenza is transmitted through the air by coughs or sneezes, creating aerosols containing the virus. Influenza can also be transmitted by direct contact with bird droppings or nasal secretions, or through contact with contaminated surfaces. Airborne aerosols have been thought to cause most infections, although the means of transmission which is most important is not absolutely clear. Influenza viruses can be inactivated by sunlight, disinfectants and detergents. As the virus can be inactivated by soap, frequent hand washing reduces the risk of infection.

Influenza spreads around the world in seasonal epidemics, resulting in the deaths of between thousands and tens of thousands of people every year, up to millions in some pandemic years. Three influenza pandemics occurred in the $20^{th}$ century and killed tens of millions of people, with each of these pandemics being caused by the appearance of a new strain of the virus in humans. Often, these new strains appear when an existing flu virus spreads to humans from other animal species, or when an existing human strain picks up new genes from a virus that usually infects birds or pigs. An avian strain named H5N1 raised the concerns of a new influenza pandemic, after it emerged in Asia in the 1990s, but it has not evolved into a form that spreads easily from human to human. In April 2009, a novel flu strain, known as influenza A/H1N1, emerged in Mexico and spread over many other nations.

In terms of virus classification, influenza viruses are RNA viruses that make up three (influenzavirus A, influenzavirus B and influenzavirus C) of the five genera of the family Orthomyxoviridae.

The genus Influenzavirus A has one species, influenza A virus. Wild aquatic birds are the natural hosts for a large variety of influenza A. Occasionally, viruses are transmitted from one to another species and may then cause devastating outbreaks or give rise to influenza pandemics. Type A viruses are the most virulent human pathogens among the three influenza types. The influenza A virus can be subdivided into different serotypes (subtypes) based on the antibody response to these viruses. The serotypes that have been confirmed in humans, ordered by the number of known human pandemic deaths, are as follows: first, H1N1 caused the Spanish flu in 1918, and the 2009 flu pandemic. H2N2 caused the Asian Flu in 1957 and H3N2 caused the Hong Kong Flu in 1968. In addition, H5N1, H7N7, H1N2, H9N2, H7N2, H7N3, and H10N7 appeared.

A more detailed description will now be given of H1N1. Influenza A (H1N1) virus (influenza A virus subtype H1N1) or simply H1N1 is the most common cause of human influenza. In addition, this subtype can infect pigs and birds.

A variant of H1N1 was responsible for the Spanish flu pandemic that killed some 50 to 100 million people worldwide over about a year in 1918 and 1919. The H1N1 genome was published in the journal of Science in 2005, reporting "When compared with today's human flu viruses, the 1918 virus had alterations in just 25 to 30 of the virus's 4,400 amino acids." Low pathogenic H1N1 strains still exist in the wild today, causing roughly half of all flu infections in 2006.

From March, 2009, the worldwide death toll from H1N1 virus increased. The influenza was first dubbed swine flu, but has since been renamed as a new flu or as the new influenza A (H1N1) in Korea because the influenza A virus subtype H1N1 cannot be spread by eating pork or pork products. The World Health Organization (WHO) officially declared the outbreak to be a pandemic on Jun. 11, 2009.

According to government statistical data, more than ten thousand cases of the new flu were generated with eight serious cases hospitalized and 14 patients dying from chronic or acute complications, as of Sep. 16, 2009.

The genus Influenzavirus B has one species, influenza B virus Influenza B almost exclusively infects humans and is less common than influenza A. The only other animals known to be susceptible to influenza B infection are the seal and the ferret. This type of influenza mutates at a rate 2-3 times slower than type A and consequently is less genetically diverse, with only one influenza B serotype. As a result of this lack of antigenic diversity, influenza B almost never causes the outbreak of a pandemic because of its limited host range.

The genus Influenzavirus C has one species, influenza C virus to which humans, dogs and pigs are susceptible Influenza C is less common than the other types A and B and usually only causes mild disease in children.

Among antiviral drugs currently available for the treatment of influenza are oseltamivir (trade name: Tamiflu), zanamivir (trade name: Relenza), peramivir and amantadine, with the predominant application of Tamiflu to the treatment of influenza A virus subtype H1N1. Tamiflu, a drug with a worldwide monopoly, was developed to treat avian influenza (AI). By blocking the activity of the viral neuraminidase enzyme, Tamiflu prevents new viral particles from being released by infected cells. An effective efficacy can be obtained when it is taken within 48 hours of the onset of symptoms. The main efficacy of Tamiflu is known to lie in the relief of symptoms, the warding off of secondary complications such as bronchitis or pneumonia, and a decrease of the latent period. Tamiflu has been used to treat and prevent influenzavirus A and influenzavirus B infections in tens of millions of people since 1999. Zanamivir, sold under the trade name of Relenza, is a neuraminidase inhibitor used in the treatment and prophylaxis of Influenzavirus A and Influenzavirus B.

Side effects associated with oseltamivir therapy include nausea and vomiting. Zanamivir shows high antiviral effects, but poor bioavailability, with fast release from the kidney.

Most of the anti-influenza agents developed thus far have side effects. Thus, there is the need for the development of an anti-influenza composition that is effective for the treatment and prophylaxis of influenza viral infection.

Commonly, influenza is spread via an airborne route, that is, when someone inhales the aerosols produced by the coughing, sneezing or spitting of an infected person. Influenza can also be spread by direct transmission, e.g., by way of the excretions, spit, snivel, or blood of infected persons. However, the spread of influenza results mostly from droplet infection such as by aerosol inhalation. Influenza viruses may be inactivated by sunlight, disinfectants, surfactants, e.g., soap, which are however not effective for the removal of airborne viruses.

The capture and inactivation of airborne viruses may lead to the effective prevention of influenza infection.

An air filter is an air-permeable member which can removes solid particulates from the air. Air filters are used in applications where air quality is important, such as in air cleaners, air conditioners, vacuum cleaners, humidifiers, dehumidifiers, etc., notably in building ventilation systems and in engines.

Designed to remove contaminants from the air, an air cleaner comprises a plurality of filters composed typically of a pretreatment filter for removing large size particles; a deodorizing filter for removing odor, volatile organic chemicals, formaldehyde, etc.; an HEPA filter for removing airborne particulates which has a diameter on the micrometer scale; and a median filter, arranged in front of the HEPA filter, for protecting the HEPA filter.

More filters may result in higher air-purifying performance, but increase resistance against overall air circulation. Accordingly, 3 to 5 filters are typically employed in an air cleaner.

Recently, studies have focused on functional filters which can selectively remove harmful materials in an elaborate manner or substitute beneficial materials for harmful materials. For example, filters for removing microparticulates with high efficiency or for purifying the airborne particulates which cause sick house syndrome have been developed.

Sumacs are shrubs and small trees in the family Anacardiaceae which grow in Asia. The trees can reach a height of some 7 meters. The sprouts produced in the Spring may be eaten after being parboiled, but care must be taken because they have toxic ingredients. Galls are produced mainly by parasitic aphids of *Melaphis chinensis*.

Leading to the present invention, intensive and thorough research into a composition acting against influenza virus, conducted by the present inventors, resulted in the finding that a sumac extract has an inhibitory activity against influenza virus and that a composition comprising the sumac extract as an active ingredient is useful in the prophylaxis of influenza viral infections and a filter coated with the extract can effectively remove airborne influenza viruses.

SUMMARY OF THE INVENTION

It is therefore an object of the present invention to provide a composition for the prevention of influenza viral infection, comprising a sumac extract.

It is another object of the present invention to provide an air filter comprising the composition.

It is a further object of the present invention to provide an air cleaner comprising the filter.

In accordance with an aspect thereof, the present invention provides a composition for the prevention of influenza viral infection, comprising a sumac extract as an active ingredient.

In a preferred embodiment, the composition may further comprise a ginkgo extract.

In another preferred embodiment, the composition may be applied to quasi-drugs.

In accordance with another aspect thereof, the present invention provides an air filter comprising the composition.

It accordance with a further aspect thereof, the present invention provides an air cleaner comprising the air filter.

DESCRIPTION OF THE PREFERRED EMBODIMENTS

The present invention addresses a composition for the prophylaxis of new influenza A (H1N1) viral infection, comprising a sumac extract as an active ingredient In an embodiment of the present invention, the composition may further comprise a ginkgo extract.

As used herein, the term "prevention" or "prophylaxis" is intended to include all actions suppressing influenzavirus infection or deterring the outbreak of influenza.

In the present invention, the influenzavirus may be directed into influenza A virus, influenza B virus or influenza C virus, with a preference for influenza A virus and a higher preference for the new influenza A (H1N1) virus.

Influenza A (H1N1) virus is a subtype of influenza A virus and is the most common cause of influenza (flu) in humans. Some strains of H1N1 are endemic to pigs (swine influenza) and to birds (avian influenza). Examples of the influenza A include A/PR/8(H1N1), A/WSN/33(H1N1), A/Bervig-Mission/1/18(rvH1N1), and A/Singapore/6/86(H1N1).

Among the new influenza A (H1N1) virus, which is responsible for the 2009 flu pandemic, are A/California/O4/09 and A/California/7/2009.

When infected with an influenza virus, patients suffer from fever, coughing, a sore throat, bronchitis, pneumonia, etc. The virus may cause an outbreak of avian flu, swine flu or goat flu.

Among the sumac trees useful in the present invention are *Rhus javanica* and *Rhus chinensis*, but the present invention is not limited thereto.

The extract may be obtained from sumac and/or ginkgo materials which may be purchased commercially, taken from nature, or cultivated artificially.

Examples of the sumac material useful in the present invention include, but are not limited to, leaves, seeds, bark, roots, as well as galls produced by parasitic aphids of *Melaphis chinensis*, with a preference for leaves, barks and the galls.

So long as it is applied to extraction from a sumac material or a ginkgo material, any method, e.g., from a simple extraction method to a method of extracting lipid-soluble ingredients may be employed in the present invention. For the convenience of extraction, the material may be pulverized first, followed by extraction with a solvent, filtration and concentration.

Examples of the extraction solvents useful in the present invention include water, ethanol, methanol, butanol, n-hexane, n-heptane, DMSO, and a combination thereof; but are not limited thereto. An artisan skilled in the art may choose a suitable extraction method depending on various factors including the amount of materials, extraction type, time, temperature, efficiency, solvents, etc. Preference is given to an extraction time of from 10 min to 1 hr and an extraction temperature of from 40 to 100° C.

In addition, the extract thus obtained may be filtered using a well-known method, such as vacuum filtration, and then concentrated by evaporation. Such a series of extraction, filtration and concentration is well known in the art. Those skilled in the art may select suitable techniques for the processes to afford a sumac or ginkgo extract.

In accordance with another embodiment of the present invention, the composition for the prophylaxis of influenzavirus infection may be applied to quasi-drugs.

With the aim of preventing infection by an influenza virus, the composition of the present invention may be used as an additive to a quasi-drug. In this regard, the composition may be used alone or in combination with another quasi-drug or ingredient in a typical manner. The amount of the composition in the quasi-drug may be determined depending on the purpose thereof.

Examples of the quasi-drug to which the composition of the present invention may be applied include a filter coating, hand-wash, mouthwash, disinfectants, shower foams, water tissues, detergent soap, humidifier fillers, masks, and aromatics.

In accordance with a further embodiment thereof, the present invention addresses an air filter comprising the composition for the prophylaxis of an influenza viral infection.

The term "air filter", as used herein, refers to a filter which functions to remove airborne microorganisms and dust and which prevents secondary contamination attributable to a filter. The air filter of the present invention may be thus applied to automobile cabins, household electric appliances, air conditioning systems, gas masks, air cleaners, and clean rooms, with a preference for air cleaners.

Further, the present invention addresses a method for manufacturing the air filter comprising the composition for the prophylaxis of influenza viral infection. The method is described below.

The method for manufacturing an air filter comprising a composition for the prophylaxis of influenzavirus infection comprises:

(a) preparing the composition for the prophylaxis of influenza viral infection;

(b) coating the air filter with the composition for the prophylaxis of an influenza viral infection; and (c) drying the coated filter.

Step (b) may be conducted by a process of immersing a roller in the composition for the prophylaxis of influenza viral infection and applying the roller to the filter base, a process of immersing a filter base in combination with a roller in the composition for the prophylaxis of influenza viral infection, and/or a process of spraying a filter base with the composition for the prophylaxis of influenza viral infection.

As the filter base, a metal, a plastic, a non-woven fabric, or a film may be used. Highly porous non-woven fabrics are preferably used in air filters for air cleaners.

Examples of the plastic include, but are not limited to, polypropylene, polyethylene, polyurethane, acryl, PVC and polystyrene, with a preference for polypropylene.

Nonwoven fabric is a sheet-like material made from long fibers, bonded together by chemical, mechanical, heat or solvent treatment. It may be divided into paper-based and fiber-based nonwoven fabric depending on the base material thereof. Examples of the nonwoven fabric material useful in the present invention include rayon, lyocell, and polypropylene, but are not limited thereto. As long as it is well known in the art, any nonwoven fabric material may be used. Preferable is polypropylene.

When taken as a filter base, a plastic resin may be melted and spun to produce filaments which are then weaved to a cloth or formed into webs, followed by binding them together into nonwoven fabric. Further, a foaming agent may be used to form a porous filter.

Above all, a composition for the prophylaxis of influenza viral infection is first prepared. Once prepared, the composition for the prophylaxis of influenza viral infection may be dissolved or diluted in a certain solvent so that it can be used in the manufacture of the air filter. The solvent may be selected from among water, ethanol, methanol, butanol, n-hexane, n-heptane, DMSO and a combination thereof.

The composition for the prophylaxis of influenza viral infection is applied to a filter base. To this end, a roller mounted with an absorbent member such as a sponge may be immersed in the composition and rolled along the filter base, followed by drying the filter base. Alternatively, the filter base may be directly immersed in the composition and dried. In another alternative, the filter base may be sprayed with the composition and dried.

The coating process may be conducted before as well as after the fibers are weaved into a filter base. In the former case, the fibers may be coated with the composition by immersing or spraying, after which they may be weaved into a filter base.

After using immersing or spraying to make a coating of the composition, the filter may be dried at room temperature or with hot wind. As long as it is well known in the art, any drying method may be employed without limitations. Because drying forces the composition to be well absorbed therein, the filter can have inhibitory activity against influenza virus for a long period of time.

In addition to the composition of the present invention, the filter according to the present invention may comprise a conventional antibacterial agent, a deodorant (e.g., a flavonoid, phytoncide, pyroligneous liquor, a plant extract, cyclodextrin, metal ion, or titanium dioxide), a dust collecting agent, etc. These agents may be applied individually or in combination, with the order of coating being subject to no particular limitation.

In accordance with a further embodiment thereof, the present invention addresses an air cleaner equipped with the air filter.

As mentioned above, an air cleaner comprises a plurality of filters. The air filter comprising the composition for the prophylaxis of influenza viral infection can be employed as a functional filter in the air cleaner.

No limitations are imparted to the type of the air cleaner to which the air filter of the present invention is applied. It may be applied to air cleaners for home, offices, and automobile cabins. Of course, the air cleaner may comprise known typical constitutional factors. Preferably, the air cleaner of the present invention comprises an air filter placed between the air intake and exhaust.

In accordance with still another embodiment thereof, the present invention addresses a method for purifying air using the air cleaner.

A better understanding of the present invention may be obtained through the following examples which are set forth to illustrate, but are not to be construed as limiting the present invention.

Preparation Example 1

Preparation of Sumac Extract

For extraction efficiency, leaves, taken from sumac trees, were dried and pulverized into powder. To 1 kg of the powder was added 5 liters of water, followed by heating at 80° C. in a water bath for 12 hrs. Filter paper was used to filter the extract thus obtained and the extract was then concentrated.

Preparation Example 2

Preparation of Ginkgo Extract

For extraction efficiency, leaves, taken from ginkgo trees, were dried and pulverized into powder. To 1 kg of the powder was added 5 liters of water, followed by heating at 80° C. in a water bath for 12 hrs. The extract thus obtained was filtered through a filter paper and concentrated.

Preparation Example 3

Manufacture of an Air Filter Coated with the Sumac Extract

The sumac extract prepared in Preparation Example 1 was diluted in water and sprayed onto a polypropylene filter base which was then dried at 140° C. for 4 min.

Preparation Example 4

Manufacture of an Air Filter Coated with a Mixture of the Sumac Extract and the Ginkgo Extract The sumac extract prepared in Preparation Example 1 was mixed 1:1 with the ginkgo extract prepared in Preparation Example 2. The mixture was diluted in water and sprayed onto a polypropylene filter base which was then dried at 140° C. for 4 min.

Experimental Example 1

Assay for Inhibitory Activity of the Sumac and the Ginkgo Extract Against Influenza Virus The sumac and the ginkgo extract obtained respectively in Preparation Examples 1 and 2 were assayed for inhibitory activity against influenza virus as follows.

Influenza A subtype H1N1 viruses A/PR/8 (H1N1) and A/WSN(H1N1) as well as the WHO standard strain influenza A (H1N1) (A/California/O4/09), which was responsible for the declaration of the 2009 pandemic, were used as the influenza virus strains to be tested.

As a sample, the sumac extract and the ginkgo extract obtained respectively in Preparation Examples 1 and 2 were used individually or in the combination of an equivalent amount.

The MDCK (Mardine Darbine Canine Kidney) cell line was inoculated at a density of $1.5 \times 10^6$ cells/mL into 6-well plates which were then incubated at 37° C. for 24 hrs in a 5% $CO_2$ atmosphere. Separately, each or a combination of the extracts was diluted to 100 mg/ml (1×) in an injection solution. The dilution was subjected to serial 10-fold dilutions. The specimens thus obtained were added in an amount of 90 µL per well to 96-well plates. 10 uL of an influenza virus sample was added to each well, incubated for 10 min, and 10-fold diluted with PBS. The MDCK cell line which had grown to confluence on the plates was infected with 1 mL of the dilution and incubated for 1 hr. For an "infection+non-administration" control, the MDCK cell line was infected with influenza virus which had not been treated with any of the extracts.

Thereafter, the medium was removed, and a mixture of 1:1 2× agarose:2×MEM containing 10 µg/ml trypsin was added in an amount of 2 mL per well. The MDCK cells were incubated at 37° C. for 2 days, fixed with 1 mL of 4% paraformaldehyde, and washed with water to remove agarose. On the next day, the cells were stained with crystal violet to count plaques and express the titer as plaque forming unit (pfu)/mL. The results are summarized in Tables 1 to 3, below.

Inhibitory Activity(%)=(1−Extract-Treated Group/Control)×100   [Equation 1]

TABLE 1

TITER OF NEW INFLUENZA A (H1N1) (A/CALIFORNIA/O4/09) AFTER TREATMENT WITH SAMPLE

| Sample | Virus Titer (pfu/ml) | Inhibitory Activity (%) |
| --- | --- | --- |
| Control | $1.9 \times 10^6$ | — |
| Sumac Extract | Not-detected | 99.99 |
| Ginkgo Extract | $1.0 \times 10^2$ | 99.99 |
| Sumac + Ginkgo Extract | Not-detected | 99.99 |

TABLE 2

TITER OF INFLUENZA A/WSN/33 (H1N1) AFTER TREATMENT WITH SAMPLE

| Sample | Virus Titer (pfu/ml) | Inhibitory Activity (%) |
| --- | --- | --- |
| Control | $3.4 \times 10^8$ | — |
| Sumac Extract | Not-detected | 99.99 |
| Ginkgo Extract | $7.0 \times 10^3$ | 99.99 |
| Sumac + Ginkgo Extract | Not-detected | 99.99 |

TABLE 3

TITER OF INFLUENZA A/PR/8 (H1N1) AFTER TREATMENT WITH SAMPLE

| Sample | Virus Titer (pfu/ml) | Inhibitory Activity (%) |
| --- | --- | --- |
| Control | $3.9 \times 10^9$ | — |
| Sumac Extract | Not-detected | 99.99 |
| Ginkgo Extract | $6.0 \times 10^2$ | 99.99 |
| Sumac + Ginkgo Extract | Not-detected | 99.99 |

As is apparent from the data of Tables 1 to 3, the groups treated with each or a combination of the sumac and the ginkgo extracts were significantly reduced in virus count compared to the control, indicating that each or a combination of the sumac and the ginkgo extracts has excellent inhibitory activity against influenza virus.

Experimental Example 2

Assay for Inhibitory Activity of the Air Filter Against Influenza Virus

The air filters coated with the sumac extract alone or in combination with the ginkgo extract, respectively manufactured in Preparation Examples 3 and 4, were assayed for inhibitory activity against influenza virus as follows.

As influenza virus strains to be tested, influenza A subtype H1N1 viruses A/PR/8 (H1N1) and A/WSN(H1N1) as well as the WHO standard strain influenza A (H1N1) (A/California/O4/09), which was responsible for the declaration of the 2009 pandemic were used.

The air filters manufactured in Preparation Examples 3 and 4 were used as samples. For control, an air filter which had not been treated with any of the extracts was used.

After being cut into a size of 2×2 cm, the filter was coated with a predetermined amount of the virus solution and incubated for 10 min so as to absorb the virus thereinto. A medium (1 mL) was loaded onto the filter which was then shaken for 10 min to wash off the virus. The filtrate was diluted to prepare specimens. 90 µL of each of the specimens was added, together with 10 µL of influenza virus, to each well of 96-well plates, followed by incubation for 10 min and 10-fold dilution with PBS. The MDCK cell line grown to confluence on the plates was infected with 1 mL of the dilution and incubated for 1 hr. For an "infection+non-administration" control, the MDCK cell line was infected with influenza virus which had been treated with none of the extracts.

Thereafter, the medium was removed, and a mixture of 1:1 2× agarose:2×MEM containing 10 μg/ml trypsin was added in an amount of 2 mL per well. The MDCK cells were incubated at 37° C. for 2 days, fixed with 1 mL of 4% paraformaldehyde, and washed with water to remove agarose. On the next day, the cells were stained with crystal violet to count plaques and express the titer as plaque forming unit (pfu)/mL.

The results are summarized in Tables 4 to 6, below.

TABLE 4

TITER OF NEW INFLUENZA A (H1N1)
(A/CALIFORNIA/O4/09) AFTER TREATMENT WITH SAMPLE

| Sample | Virus Titer (pfu/ml) | Inhibitory Activity (%) |
|---|---|---|
| Control | $1.9 \times 10^6$ | — |
| Air Filter Coated with Sumac Extract alone | Not-detected | 99.99 |
| Air Filter Coated with Sumac and Ginkgo Extracts | Not-detected | 99.99 |

TABLE 5

TITER OF INFLUENZA A/WSN/33 (H1N1)
AFTER TREATMENT WITH SAMPLE

| Sample | Virus Titer (pfu/ml) | Inhibitory Activity (%) |
|---|---|---|
| Control | $3.4 \times 10^8$ | — |
| Air Filter Coated with Sumac Extract alone | Not-detected | 99.99 |
| Air Filter Coated with Sumac and Ginkgo Extracts | Not-detected | 99.99 |

TABLE 6

TITER OF INFLUENZA A/PR/8 (H1N1)
AFTER TREATMENT WITH SAMPLE

| Sample | Virus Titer (pfu/ml) | Inhibitory Activity (%) |
|---|---|---|
| Control | $3.9 \times 10^9$ | — |
| Air Filter Coated with Sumac Extract alone | Not-detected | 99.99 |
| Air Filter Colated with Sumac and Ginkgo Extracts | Not-detected | 99.99 |

The data of Tables 4 to 6 demonstrate that the air filter treated with the sumac extract alone or in combination with the ginkgo extract has excellent inhibitory activity against the influenza virus.

Having high inhibitory activity against influenza virus, as described hitherto, the composition comprising a sumac extract in accordance with the present invention can be applied to the prevention of influenza viral infection. Hence, a filter coated with the composition can remove influenza virus from the air so that it can be employed in an air cleaner for the prophylaxis of new influenza viral infection.

Although the preferred embodiments of the present invention have been disclosed for illustrative purposes, those skilled in the art will appreciate that various modifications, additions and substitutions are possible, without departing from the scope and spirit of the invention as disclosed in the accompanying claim.

What is claimed is:

1. An air filter comprising a composition comprising an effective amount of a hot water extract of sumac leaves, wherein the air filter comprising said composition captures and inactivates influenza virus A/California/04/09.

2. The air filter of claim 1, wherein said air filter comprising said composition is obtained by:
   preparing the composition comprising the hot water extract of sumac leaves;
   coating a filter base of an air filter with said composition to provide a composition-coated filter base; and
   drying the composition-coated filter base,
   wherein the air filter base is coated by:
   immersing a roller in the composition comprising the hot water extract of sumac leaves and applying the roller comprising the composition to the filter base;
   immersing the filter base in combination with a roller into the composition; and/or
   spraying the filter base with the composition.

3. The air filter of claim 2, wherein the filter base is plastic or a nonwoven fabric.

4. The air filter of claim 3, wherein the nonwoven fabric is a paper-based nonwoven fabric or a fiber-based nonwoven fabric.

5. An air cleaner comprising the air filter of claim 1.

6. A method of using the air filter in claim 1 to inactivate an influenza virus, comprising contacting the air filter with the influenza virus, wherein the influenza virus is influenza A/California/04/09.

7. A method of using the air cleaner of claim 5 to inactivate an influenza virus, comprising contacting the air cleaner with the influenza virus, wherein the influenza virus is influenza A/California/04/09.

8. A method for treating an influenza virus virus in a human in need thereof, comprising administering a composition comprising an effective amount of a hot water extract of sumac leaves to said human, wherein the influenza virus is influenza A/California/04/09, and wherein the composition is in the form of a quasi-drug.

9. The method of claim 8, wherein the composition further comprises an aqueous extract of ginkgo leaves.

10. The method of claim 8, wherein the quasi-drug is selected from a filter coating agent, a hand-wash, a mouth-wash, a disinfectant, a shower foam, a water tissue, a detergent soap, a humidifier filler, a mask, and an aromatic.

* * * * *

UNITED STATES PATENT AND TRADEMARK OFFICE
CERTIFICATE OF CORRECTION

PATENT NO.         : 9,119,814 B2                                       Page 1 of 1
APPLICATION NO.    : 12/789331
DATED              : September 1, 2015
INVENTOR(S)        : Hyoung Joon Kim et al.

It is certified that error appears in the above-identified patent and that said Letters Patent is hereby corrected as shown below:

In the claims

Column 10, Line 44:
"8. A method for treating an influenza virus virus in a human" should read, --8. A method for treating an influenza virus in a human--.

Signed and Sealed this
Second Day of August, 2016

Michelle K. Lee
*Director of the United States Patent and Trademark Office*